US011123536B2

(12) United States Patent
Follman et al.

(10) Patent No.: US 11,123,536 B2
(45) Date of Patent: Sep. 21, 2021

(54) ANTIMICROBIAL CAP FOR DISINFECTING A PORT AND METHOD

(71) Applicant: PROFESSIONAL DISPOSABLES INTERNATIONAL, INC., Orangeburg, NY (US)

(72) Inventors: Mark Follman, Glen Rock, NJ (US); John Tanayan, Ridgefield Park, NJ (US); Kathryn Spencer, San Diego, CA (US); Jesse R. Dlugos, Woodbridge, CT (US); Jeffrey E. Ransden, Fairfield, CT (US)

(73) Assignee: PROFESSIONAL DISPOSABLES INTERNATIONAL, INC., Orangeburg, NY (US)

( * ) Notice: Subject to any disclaimer, the term of this patent is extended or adjusted under 35 U.S.C. 154(b) by 649 days.

(21) Appl. No.: 15/917,128

(22) Filed: Mar. 9, 2018

(65) Prior Publication Data
US 2018/0256883 A1   Sep. 13, 2018

Related U.S. Application Data

(60) Provisional application No. 62/469,336, filed on Mar. 9, 2017.

(51) Int. Cl.
*A61L 2/00* (2006.01)
*B08B 3/04* (2006.01)
*A61M 5/32* (2006.01)
*A61M 39/18* (2006.01)
*A61M 39/16* (2006.01)
(Continued)

(52) U.S. Cl.
CPC .............. *A61M 39/18* (2013.01); *A01N 25/30* (2013.01); *A01N 47/44* (2013.01); *A61L 2/18* (2013.01);
(Continued)

(58) Field of Classification Search
CPC ........ A61L 2/0082; A61L 2/0088; A61L 2/16; A61L 2/18; A61L 2101/00; A61L 2202/23; A61L 2202/24; A61L 2300/00; A61K 9/00; A61J 1/00; A61J 3/00; A61B 19/34; A61M 39/16; A61M 39/20
(Continued)

(56) References Cited

U.S. PATENT DOCUMENTS 7,282,186 B2    10/2007  Lake, Jr. et al.
D607,325 S      1/2010   Rogers et al.
(Continued)

FOREIGN PATENT DOCUMENTS

WO    WO 2016/044821 A1    3/2016

OTHER PUBLICATIONS

U.S. Appl. No. 15/916,891, filed Mar. 9, 2018.

*Primary Examiner* — Monzer R Chorbaji
(74) *Attorney, Agent, or Firm* — Baker Botts L.L.P.

(57) ABSTRACT

An antimicrobial cap and method for inhibiting the growth of microbes and disinfecting a port are disclosed. The antimicrobial cap comprises an assembly that includes an outer cap, an inner member and a pad disposed within the inner member and impregnated with an antimicrobial agent in order to disinfect the port. The antimicrobial cap includes attachment features and a lock out mechanism allowing the disinfection of different types of ports and connectors and their safe disengagement and thereafter enabling the lock out mechanism in order to prevent re-use of the antimicrobial cap.

20 Claims, 16 Drawing Sheets

(51) Int. Cl.
*A61M 39/20* (2006.01)
*A01N 47/44* (2006.01)
*A61L 2/23* (2006.01)
*A01N 25/30* (2006.01)
*A61L 2/18* (2006.01)
*B65D 75/36* (2006.01)
*A61M 39/02* (2006.01)

(52) U.S. Cl.
CPC ............ *A61L 2/23* (2013.01); *A61M 39/162* (2013.01); *A61M 39/20* (2013.01); *A61L 2202/24* (2013.01); *A61M 2039/0285* (2013.01); *A61M 2039/0288* (2013.01); *A61M 2205/0205* (2013.01); *A61M 2205/273* (2013.01); *A61M 2209/06* (2013.01); *B65D 75/367* (2013.01)

(58) Field of Classification Search
USPC ........ 422/544–546, 292, 300; 604/192, 187; 134/104.1
See application file for complete search history.

(56) References Cited

U.S. PATENT DOCUMENTS

| | | | |
|---|---|---|---|
| 8,419,713 | B1 | 4/2013 | Solomon et al. |
| 8,740,864 | B2* | 6/2014 | Hoang ................. A61M 39/02 604/267 |
| 8,999,073 | B2* | 4/2015 | Rogers .................... A61L 2/18 134/115 R |
| 9,283,369 | B2 | 3/2016 | Ma et al. |
| 9,352,140 | B2 | 5/2016 | Kerr et al. |
| 2007/0018014 | A1* | 1/2007 | Finell .................... A47K 3/005 239/288 |
| 2011/0217212 | A1* | 9/2011 | Solomon ............ A61M 39/165 422/292 |
| 2012/0302997 | A1 | 11/2012 | Gardner et al. |
| 2014/0358115 | A1 | 12/2014 | Chelak et al. |
| 2015/0217106 | A1 | 8/2015 | Banik et al. |
| 2015/0314120 | A1 | 11/2015 | Gardner |
| 2016/0144118 | A1 | 5/2016 | Solomon et al. |
| 2017/0056640 | A1 | 3/2017 | Tennican |

* cited by examiner

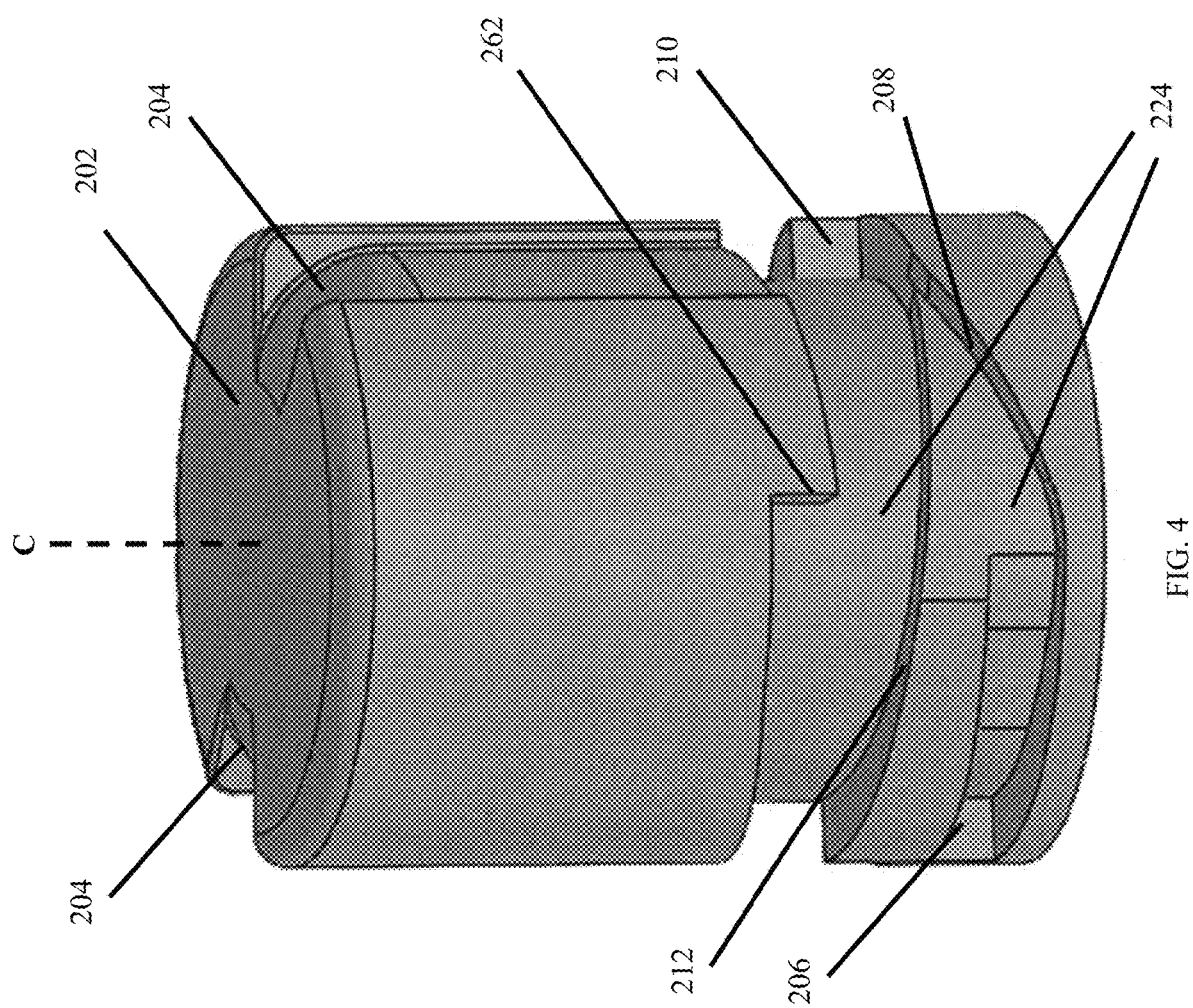

Section A-A

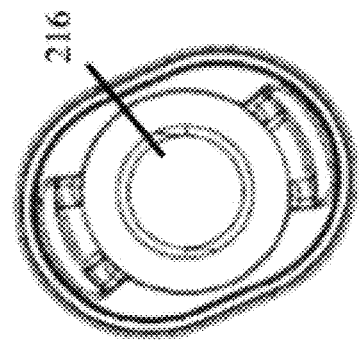
FIG. 7C
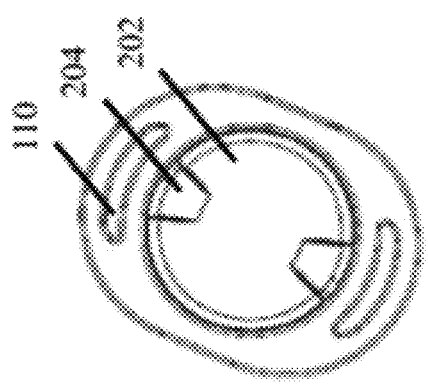
FIG. 7B
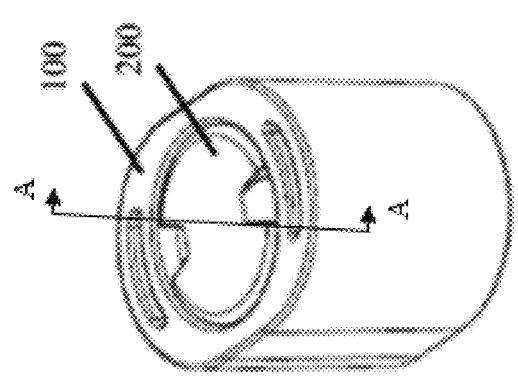
FIG. 7A
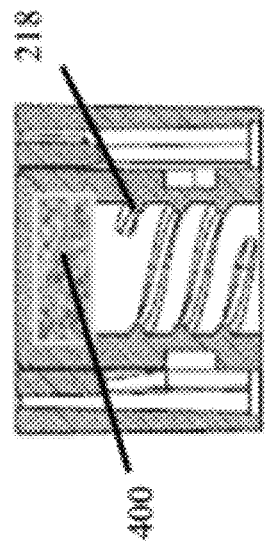
FIG. 7E
FIG. 7D

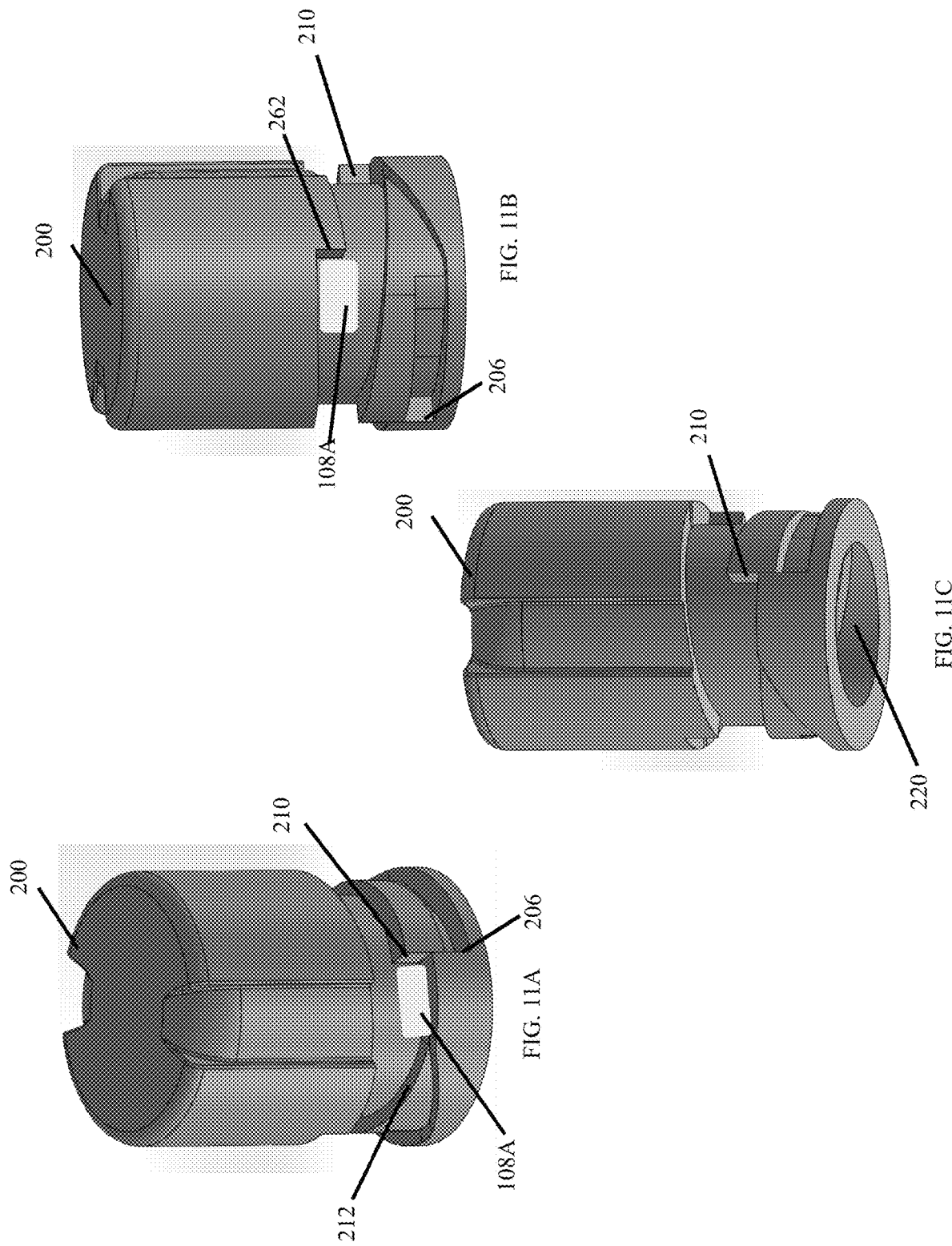

ANTIMICROBIAL CAP FOR DISINFECTING A PORT AND METHOD

CROSS-REFERENCE TO RELATED APPLICATIONS

This application claims priority to U.S. Provisional Application No. 62/469,336, filed on Mar. 9, 2017, the contents of which is hereby incorporated by reference in its entirety.

FIELD OF THE DISCLOSED SUBJECT MATTER

The disclosed subject matter relates to an antimicrobial cap. Specifically, the anti-microbial cap is attachable to a port to disinfect the port and the cap is thereafter disabled in order to prevent re-use of the antimicrobial cap.

BACKGROUND OF THE DISCLOSED SUBJECT MATTER

A variety of caps that are commonly used to treat ports and other medical connectors typically include an open end, a closed end and a cavity in which the port is attached. Furthermore, the cavity can include a foam or non-woven material having a disinfecting solution that cleans the port when they come to contact. Examples of medical connectors for which such caps are used are intravascular connectors associated with a fluid pathway, such as a central line, connectors associated with an IV bag, luer lock connectors and others. These connectors require careful handling and disinfection prior to use on a port connected to a patient since the use of various fluid reservoirs can increase the risk of infections due to possible contamination factors relating to frequent use and fluid transfer. However, in many cases the provided caps need to be manufactured for specific connectors and must include additional structures such as threads to be able to securely engage the medical connectors and/or ports. Further, such caps lack any indication or disabling feature to prevent a user from reusing the cap a subsequent time. Therefore, it would be an advantage to have a cap that can be used to provide protection for different types of medical connectors/ports, and have an indicator to prevent re-use.

Thus, there remains a continued need for an efficient and safe antimicrobial cap for cleaning and disinfecting a port that includes a disabling feature to ensure that the antimicrobial cap is non-reusable. The presently disclosed subject matter satisfies these and other needs.

SUMMARY OF THE DISCLOSED SUBJECT MATTER

The purpose and advantages of the disclosed subject matter will be set forth in and are apparent from the description that follows, as well as will be learned by practice of the disclosed subject matter. Additional advantages of the disclosed subject matter will be realized and attained by the devices particularly pointed out in the written description and claims hereof, as well as from the appended drawings.

To achieve these and other advantages and in accordance with the purpose of the disclosed subject matter, as embodied and broadly described, the disclosed subject matter includes an antimicrobial cap to treat a port, the antimicrobial cap comprising an outer cap having a first end, a second end and defining a cavity therein, the outer cap having a sidewall with an inner surface that defines an engagement structure. An inner member is receivable in the outer cap comprising an open end, a closed end and defining a chamber therein, the inner member having a sidewall with an interior surface and an exterior surface, wherein the interior surface is engageable with a port, the exterior surface defining an attachment feature configured to engage with the engagement structure of the outer cap, the attachment feature at least including a first stop, a second stop, and a first ramp there between, wherein the engagement structure abuts the first stop in a first position to permit rotational movement of the antimicrobial cap in a first direction with respect to the port and to engage the inner member with the port, wherein the engagement structure is movable with respect to the inner member along the first ramp in a second direction and abuts the second stop in a second position to rotate the antimicrobial cap with respect to the port and to release the antimicrobial cap from the port, wherein the engagement structure is movable along a second ramp of the attachment feature upon further rotating the antimicrobial cap in the first direction such that the engagement structure is prevented from further movement along the first ramp, and a pad disposed within the chamber of the inner member and impregnated with an antimicrobial agent, wherein the port is receivable in the chamber with the interior surface engaged thereto, wherein the pad is compressed by the port to release the antimicrobial agent therefrom.

In accordance with another aspect of the disclosed subject matter, a method of inhibiting the growth and disinfecting a port is provided. Specifically, the disclosed subject matter comprises providing an antimicrobial cap having an outer cap having a first end, a second end and defining a cavity therein, the outer cap having a sidewall with an inner surface that defines an engagement structure, an inner member receivable in the outer cap comprising an open end, a closed end and defining a chamber therein, the inner member having a sidewall with an interior surface and an exterior surface, wherein the interior surface is engageable with a port, the exterior surface defining an attachment feature configured to engage with the engagement structure of the outer cap, the attachment feature at least including a first stop, a second stop, and a first ramp there between, wherein the engagement structure abuts the first stop in a first position, a pad disposed within the chamber of the inner member, the pad impregnated with an antimicrobial agent. Rotating the antimicrobial cap in a first direction with respect to the port to engage the inner member with the port, wherein the port is receivable in the chamber with the interior surface engaged thereto, compressing the pad by the port to release the antimicrobial agent therefrom, moving the engagement structure along the first ramp in a second direction and abutting the second stop in a second position; and rotating the antimicrobial cap with respect to the port and to release the antimicrobial cap from the port.

It is to be understood that both the foregoing general description and the following detailed description and drawings are examples and are provided for purpose of illustration and not intended to limit the scope of the disclosed subject matter in any manner.

The accompanying drawings, which are incorporated in and constitute part of this specification, are included to illustrate and provide a further understanding of the devices of the disclosed subject matter. Together with the description, the drawings serve to explain the principles of the disclosed subject matter.

BRIEF DESCRIPTION OF THE DRAWINGS

The subject matter of the application will be more readily understood from the following detailed description when read in conjunction with the accompanying drawings, in which:

FIG. 4 is a side perspective view of the inner member of FIG. 1 in accordance with the disclosed subject matter.

FIG. 7A is a top perspective view of the antimicrobial cap of FIG. 1 in accordance with the disclosed subject matter.

FIG. 7B is a top plan view of the antimicrobial cap of FIG. 7A in accordance with the disclosed subject matter.

FIG. 7C is a bottom plan view of the antimicrobial cap of FIG. 7A in accordance with the disclosed subject matter.

FIG. 7D is a side view of the antimicrobial cap of FIG. 7A in accordance with the disclosed subject matter.

FIG. 7E is a side cross-sectional view of the antimicrobial cap of FIG. 7D along lines A-A in accordance with the disclosed subject matter.

FIG. 11A is a side perspective view of the inner member of FIG. 10A rotated counterclockwise in accordance with the disclosed subject matter.

FIG. 11B is a side perspective view of the inner member of FIG. 11A further rotated counterclockwise in accordance with the disclosed subject matter.

FIG. 11C is a bottom perspective view of the inner member of FIG. 11B further rotated in accordance with the disclosed subject matter.

DETAILED DESCRIPTION

Figure 1:
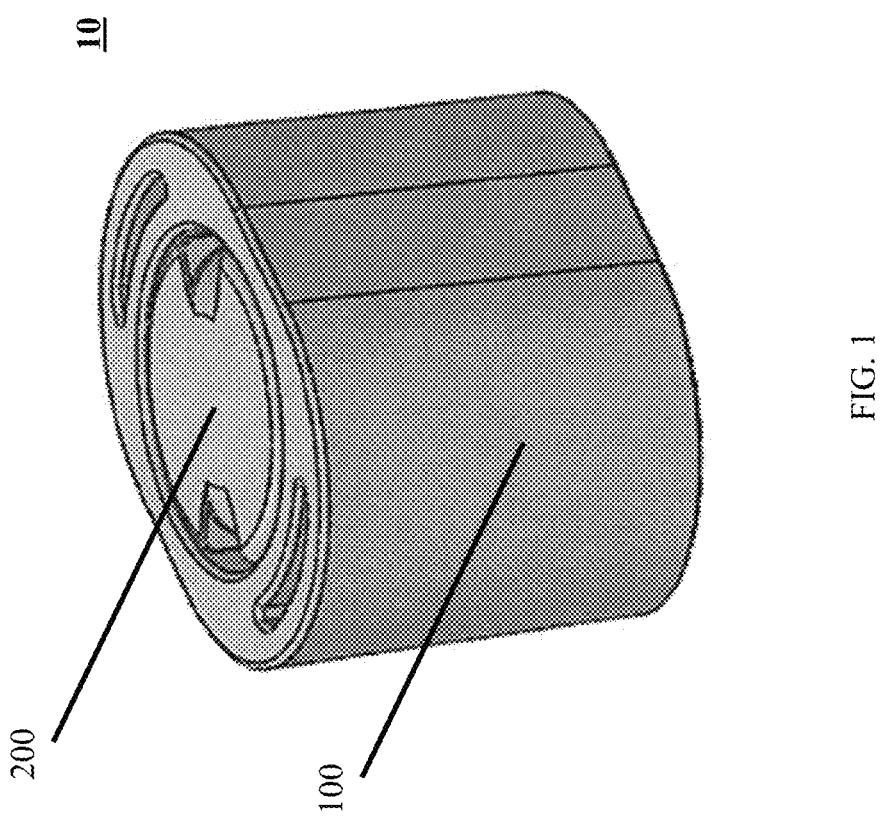
FIG. 1 is a top perspective view of an antimicrobial cap in accordance with the disclosed subject matter.

Reference will now be made in detail to embodiments of the disclosed subject matter, an example of which is illustrated in the accompanying drawings. The disclosed subject matter will be described in conjunction with the detailed description of the system.

The terms used in this specification generally have their ordinary meanings in the art, within the context of this subject matter and in the specific context where each term is used. Certain terms are defined below to provide additional guidance in describing the compositions and methods of the disclosed subject matter and how to make and use them.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to systems or processes, the term can mean within an order of magnitude, preferably within 5-fold, and more preferably within 2-fold, of a value.

As disclosed herein, the antimicrobial cap presented herein can be used for inhibiting the growth of microbes and/or disinfecting a port. The antimicrobial cap includes an outer cap, inner member and a pad that contains an antimicrobial agent e.g., a solution that disinfects a medical port upon contact. The aforementioned port can include access ports on tubing sets (extension sets, T-connectors and IV sets), access ports on catheters, valves, luer connectors, stethoscopes and other connecting components or devices whereby disinfection is desired.

In accordance with the disclosed subject matter, an antimicrobial cap having an outer cap, an inner member and a pad that is impregnated with an antimicrobial element such as, for example, a disinfecting solution is provided. The pad can be disposed within a chamber of the inner member and the inner member can be disposed within the outer cap such that the port is receivable within the chamber of the inner member to engage the pad. Specifically, the outer cap has a first end and a second end that defines a cavity. Furthermore, the outer cap has a sidewall with an exterior surface and an inner surface that includes an engagement structure in order to engage the inner member of the antimicrobial cap. The inner member is receivable in the outer cap and has an open end and a closed end that defines a chamber. Furthermore, the inner member also has a sidewall with an interior surface and an exterior surface, wherein the interior surface is engageable with a port and the exterior surface defines an attachment feature configured to engage with the engagement structure of the outer cap. This attachment feature includes a first stop, a second stop, and a first ramp there between. As such, when the antimicrobial cap is in a first position, the engagement structure of the cap abuts the first stop in order to permit rotational movement of the antimicrobial cap in a first direction with respect to the port and to engage the inner member with the port. In addition, the engagement structure is movable along the first ramp in a second direction and abuts the second stop in a second position in order to rotate the antimicrobial cap with respect to the port and to release the antimicrobial cap from the port. The engagement structure of the outer cap is movable along a second ramp of the attachment feature upon further rotation of the antimicrobial cap in the first direction such that the engagement structure is prevented from further movement along the first ramp.

Solely for purpose of illustration, an exemplary embodiment of an antimicrobial cap, is shown schematically in FIG. 1. The examples herein are not intended to limit the scope of the disclosed subject matter in any manner. Particularly, and as illustrated, an assembled antimicrobial cap 10 is shown having an outer cap 100, inner member 200 and pad (not shown). Specifically, when antimicrobial cap 100 is in a use position, the inner member 200 is disposed inside the outer cap 100 in order to engage the port of a medical device and the pad is fully disposed within inner member 200. In some embodiments, the outer cap 100 has a first end and a second end such that the second end of the inner member 200 is visible and accessible through the outer cap 100, as shown in FIG. 1. In some embodiments, the first end of outer cap 100 can be an open end. In some embodiments, the second end of the outer cap 100 can be closed or partially closed.

Figure 2:
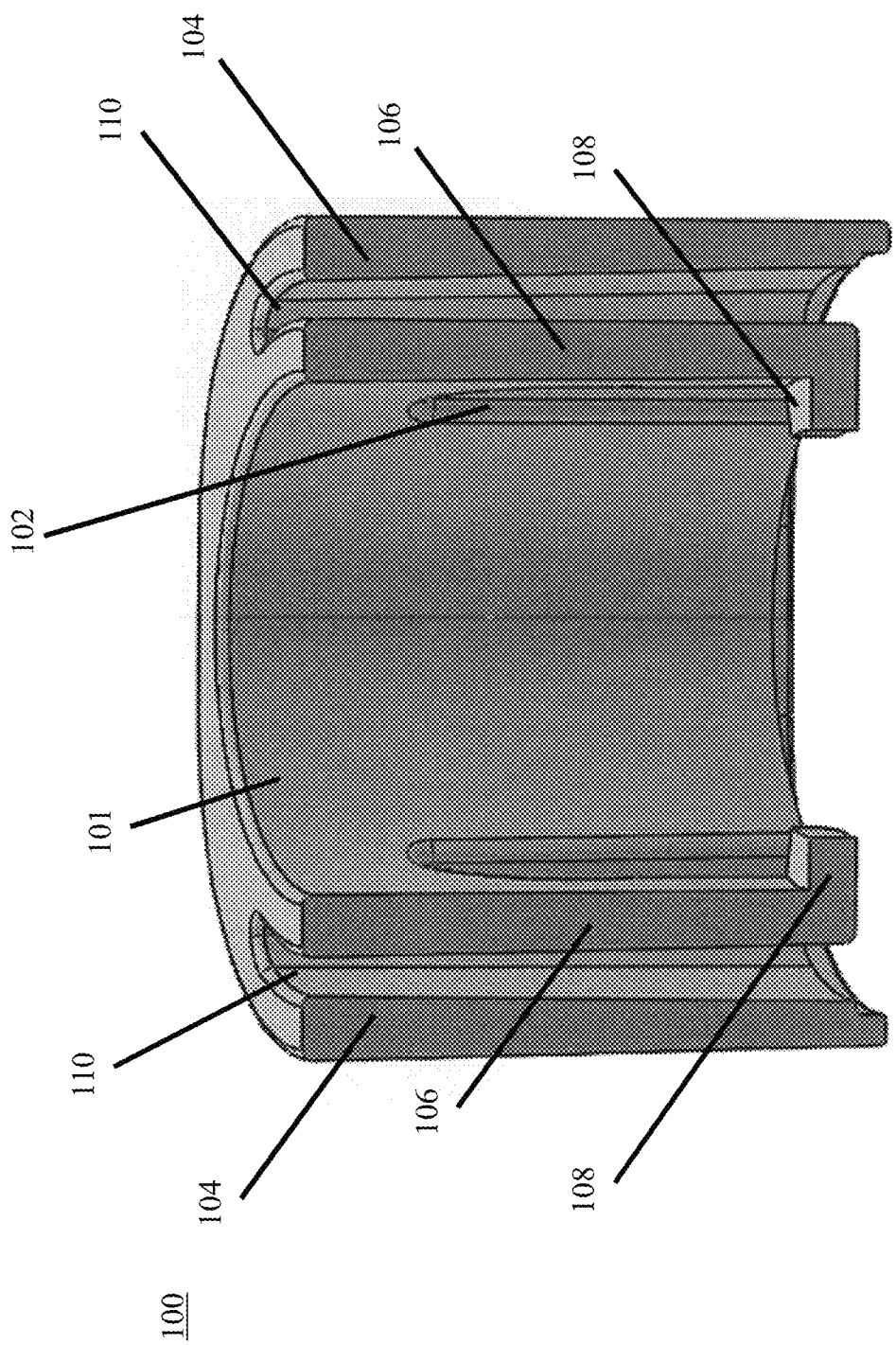
FIG. 2 is a side cross-sectional perspective view of the outer cap of FIG. 1 in accordance with the disclosed subject matter.

FIG. 2 shows a side cross-sectional perspective view of outer cap 100 along a transverse center axis across a width of the outer cap, the not-shown portion of the outer cap being symmetrical about the axis. The outer cap has an inner surface 101 that includes engagement structures. The inner surface defines recesses 102 that extend along at least a portion of the length of the inner surface 101. The recesses 102 define a flexural finger 106 extending across the length of the outer cap 100. As the outer cap is symmetrical about the transverse axis, the flexural finger 106 is defined by four recesses, wherein two recesses are at respective sides of the finger 106. Each respective finger 106 is further defined by a slot 110 at a back side thereof to permit the flexural finger the flexibility to move inward and outward of the cavity. The slot 110 is disposed between the back wall 104 and the flexural finger 106. In some embodiments flexural finger 106 can also include protrusion 108 that engages the inner member 200, as further discussed herein. The flexural finger 106 can be of any suitable width.

Figure 3C:
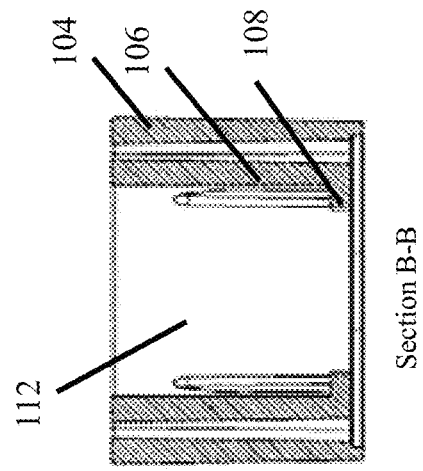
FIG. 3C is a side cross-sectional view of the outer cap of FIG. 3B along lines B-B in accordance with the disclosed subject matter.
Figure 3F:
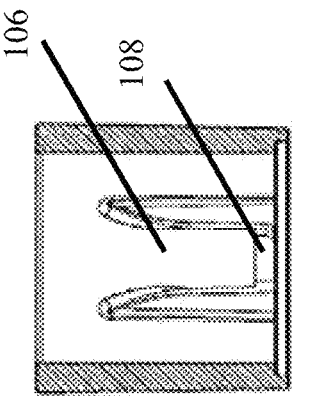
FIG. 3F is a side cross-sectional view of the outer cap of FIG. 3E along lines A-A in accordance with the disclosed subject matter.
Figure 3B:
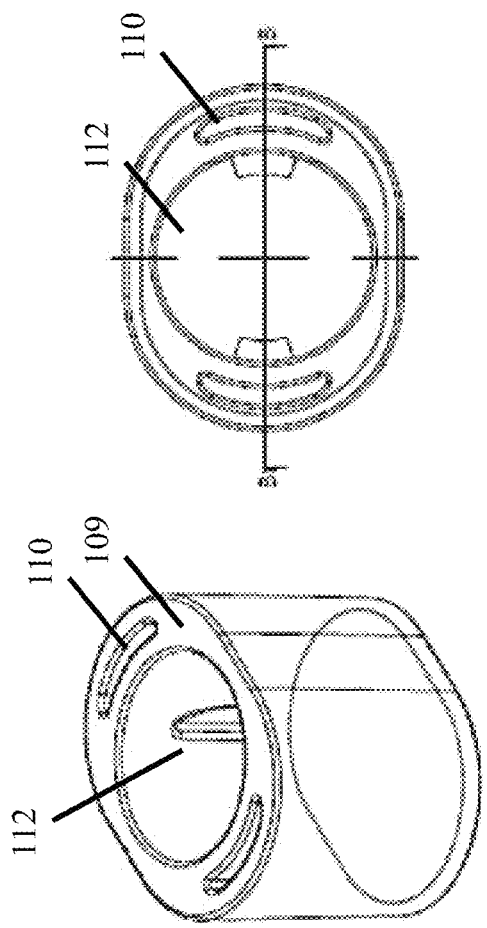
FIG. 3B is a top plan view of the outer cap of FIG. 1 in accordance with the disclosed subject matter.
Figure 3E:
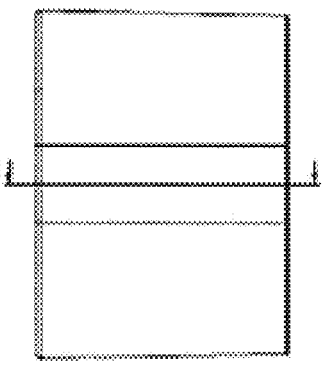
FIG. 3E is a side view of the outer cap of FIG. 1 in accordance with the disclosed subject matter.
Figure 3A:
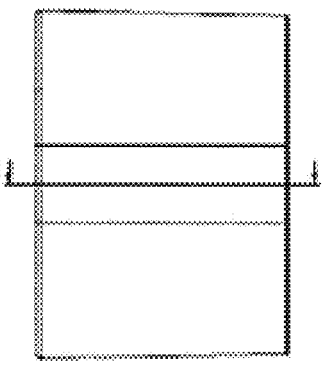
FIG. 3A is a top perspective view of the outer cap of FIG. 1 in accordance with the disclosed subject matter.

Solely for purpose of illustration, reference is now made to FIGS. 3A-3F showing various views and cross-sections of outer cap 100 in accordance with the disclosed subject matter. FIG. 3A shows a top perspective view of outer cap 100 that receives inner member (not shown). A second end 109 of the outer cap is shown in FIG. 3A. FIG. 3B is a top view of the outer cap 100 showing cavity 112 and slot 110 and includes lines B-B that represent the view of FIG. 3C. Specifically, FIG. 3C shows a side cross-sectional view of outer cap 100 along cross-sectional lines B-B, as referenced in connection to FIG. 3B. FIG. 3C depicts a similar view as FIG. 2. As shown, the outer cap 100 includes at least one flexural finger 106 extending along a length of the outer cap 100. In some embodiments, the flexural finger 106 includes a protrusion 108 that engages the inner member 200. The protrusion 108 is located at a distal end of the flexural finger 106.

Figure 3D:
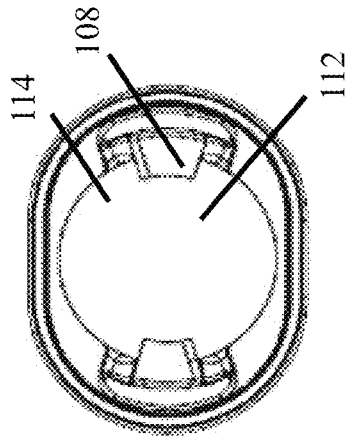
FIG. 3D is a bottom plan view of the outer cap of FIG. 1 in accordance with the disclosed subject matter.

FIG. 3D shows a bottom plan view of outer cap 100. Specifically, the first end 114 and protrusions 108 are illustrated such that they extend inwardly from the inner surface 101 of the outer cap 100 and into the cavity 112. FIG. 3E shows a side view of outer cap 100 and includes lines A-A that represent the view of FIG. 3F. Specifically, FIG. 3F shows a side cross-sectional view of outer cap 100 along cross-sectional lines A-A, as referenced in connection to FIG. 3E. As shown, the outer cap 100 includes a flexural finger 106 extending along a length of the outer cap 100. The outer cap can comprise any suitable material such as, but not limited to, plastic, polymer (e.g., MDPE), silicone or any other suitable material that can be molded, machined, cast and/or by layered manufacturing such as 3D printing.

FIG. 4 shows a side perspective view of the inner member 200. Specifically, the inner member 200 has a closed end 202 and an open end (not shown) that defines a chamber therein. In some embodiments, the inner member 200 has an interior surface 220 (as depicted in FIG. 11C) that engages a port using, for example, a set of female threads or any other suitable engagement structure. The inner member 200 has an exterior surface that has one or more attachment features that can engage with the engagement structure of the outer cap 100. The one or more attachment features can include a first stop 206, a second stop 210 and a first ramp 208 there between, as shown in FIG. 4. In addition, the one or more attachment features can include a second ramp 212 and a third stop 262. In some embodiments, the first stop 206, the second stop 210, the first ramp 208 and the second ramp 212 extend at different radial distances from a vertical center axis C. The attachment features can define one or more recessed exterior surfaces 224 that can also extend at different radial distances from a vertical center axis C. The one or more recessed exterior surfaces 224 can remain in contact with protrusion 108 of flexural finger 106, as further discussed herein. In some embodiments, the one or more attachment features of inner member 200 are symmetrical about a longitudinal center of the inner member e.g., axis C and the respective first and second stops can be distanced from each other by approximately 180° or any other suitable angle. In some embodiments, the first ramp 208 is radially distanced further from axis C than the second ramp 212 in order to permit initial engagement of the engagement structure of the outer cap 100 with the inner member. Furthermore, the one or more attachment features of the inner member 200 can include one or more recessed surfaces 204 that extend longitudinally along the exterior surface of the inner member 200 from the closed end 202. The recessed surfaces 204 of the inner member 200 facilitate the assembly of the flexible finger 106 and protrusion 108 of the outer cap 100 during the inseparable assembly of the inner member 200 into the outer cap 100. In some embodiments, the one or more recessed surfaces 204 can be of any suitable width in order to facilitate the engagement structure with the outer cap 100. The inner member 200 can be made with any suitable material. For example, it can be made out of plastic, polymer (e.g., MDPE), silicone or any other suitable material that can be molded, machined, cast and/or by layered manufacturing such as 3D printing.

Figure 5A:
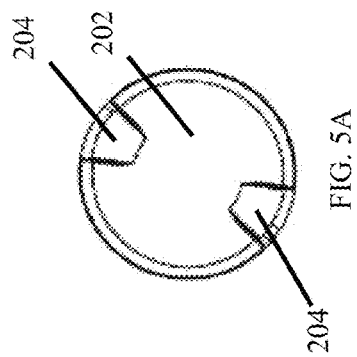
FIG. 5A is a top view of the inner member of the antimicrobial cap of FIG. 1 in accordance with the disclosed subject matter.
Figure 5C:
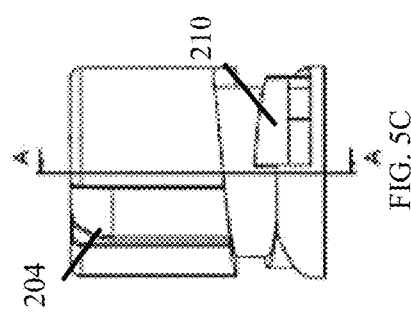
FIG. 5C is another side view of the inner member of the antimicrobial cap of FIG. 1 in accordance with the disclosed subject matter.
Figure 5E:
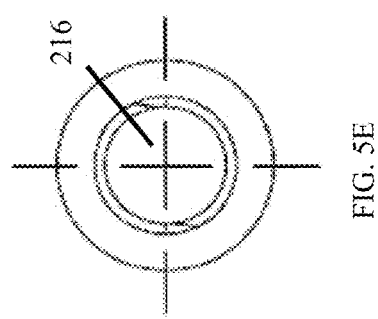
FIG. 5E is a bottom view of the inner member of FIG. 5C in accordance with the disclosed subject matter.
Figure 5D:
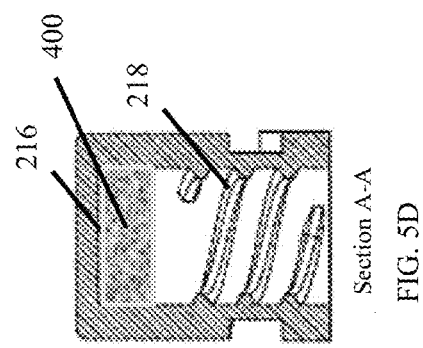
FIG. 5D is a side cross-sectional view of the inner member of FIG. 5C along lines A-A in accordance with the disclosed subject matter.
Figure 5B:
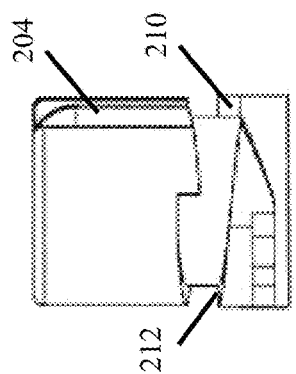
FIG. 5B is a side view of the inner member of the antimicrobial cap of FIG. 1 in accordance with the disclosed subject matter.

Solely for purpose of illustration, reference is now made to FIGS. 5A-5F showing various views and cross-sections of inner member 200 in accordance with the disclosed subject matter. FIG. 5A shows a top view of inner member 200 including the closed end 202 and the recessed surfaces 204. FIG. 5B shows a side view of inner member 200 with the recessed surface 204 extending from the closed end and the second ramp 212 is shown. FIG. 5C shows a side view of the inner member 200 along with cross-sectional lines A-A as referenced in connection to FIG. 5D. Specifically, FIG. 5D shows a cross-sectional view of the interior surface of the inner member 200 that can include a set of female threads 218 disposed in the chamber thereof that are capable of engaging the port and can include a pad 400 therein Furthermore, FIG. 5E shows a bottom view of inner member 200 including chamber 216 that receives the port for disinfection.

Figure 6:
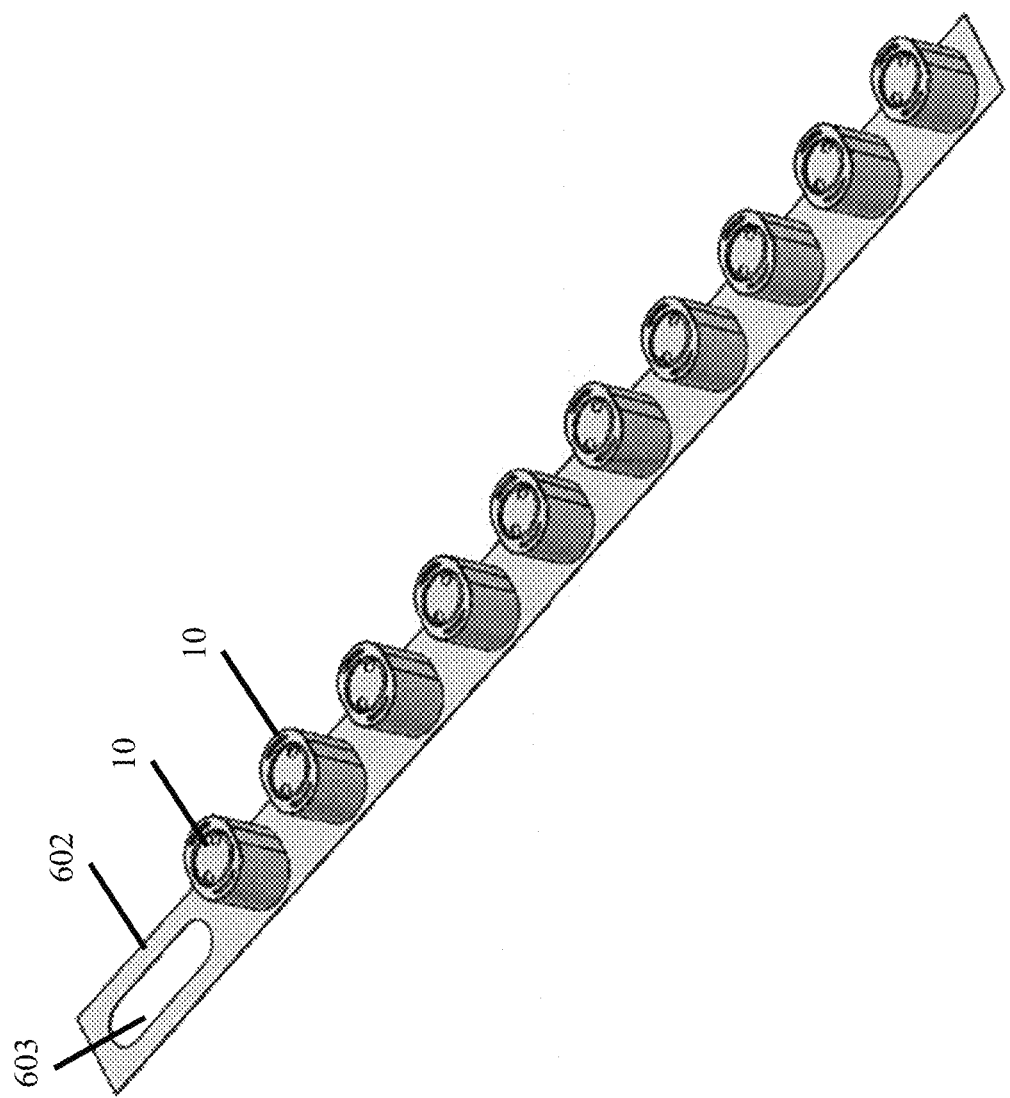
FIG. 6 is a side perspective view of packaging for the antimicrobial cap of FIG. 1, in accordance with the disclosed subject matter.

Solely for purpose of illustration, reference is now made to FIG. 6 showing a side perspective view of packaging for a plurality of antimicrobial caps in accordance with the disclosed subject matter. Specifically, FIG. 6 shows a plurality of antimicrobial caps 10 each of them sealed with a strip 602 and in a ready condition. In some embodiments, the strip 602 can include a sealable adhesive polymer laminate to ensure that the antimicrobial caps are securely placed on strip 602. In other embodiments, the antimicrobial cap includes a lid that is attached to the strip 602. In some embodiments, the strip 602 can be sealed to a rim of outer cap 100 or a rim of inner member 200 or both to seal the cavity of the antimicrobial cap from the external environment. The strip 602 allows for individually packaged antimicrobial cap to disengage from the strip for individual use. The strip can define a hole 603 for hanging/storage purposes. In the ready condition, the antimicrobial cap can be packaged with the strip 602 and can be transported/shipped in a ready to use state. The strip 602 can include any suitable material such as but not limited to sealable adhesive layered foil, aluminum and/or laminated polymer lidding film. In other embodiments, the antimicrobial cap can be individually sealed with a lid (not shown) and not include a strip 602. Such suitable lids are further described in U.S. application Ser. No. 15/916,891 entitled "Method and Antimicrobial Cap for Disinfecting A Port" filed on the same day as this application, the contents of which is incorporated by reference in its entirety.

FIGS. 7A-7D show various views and cross-sections of the antimicrobial cap 10 in accordance with some embodiments of the disclosed subject matter. FIG. 7A shows a top perspective view of antimicrobial cap 10 including the outer cap 100 and the inner member 200 along with cross-sectional lines A-A as referenced in connection to FIG. 7E. FIG. 7B is a top plan view of the antimicrobial cap 10 including closed end 202 and recessed surfaces 204 of inner member 200. Furthermore, FIG. 7B is a top plan view that shows the slots 110. FIG. 7C shows a bottom plan view of antimicrobial cap 10 including chamber 216 that receives the port for disinfection. FIG. 7D shows a side view of antimicrobial cap 10. FIG. 7E shows a side cross-sectional view of the antimicrobial cap 10 along cross-sectional lines A-A as referenced in connection to FIG. 7A with a pad 400 therein. As shown, the inner member 200 is disposed in the outer cap 100 and the interior surface of inner member 200 can include a set of female threads 218 for engaging the port.

Figure 8B:
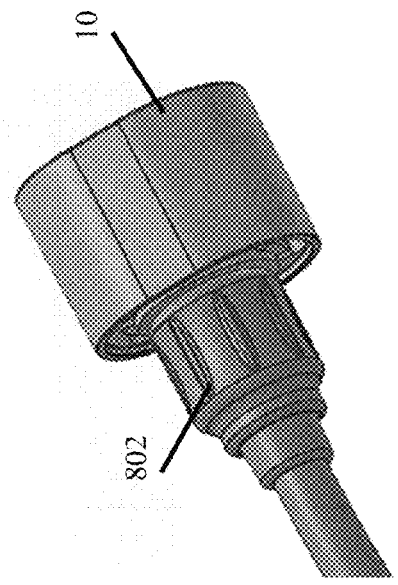
FIG. 8B is a side perspective view of the antimicrobial cap of FIG. 1 engaging a medical port, in accordance with the disclosed subject matter.
Figure 8D:
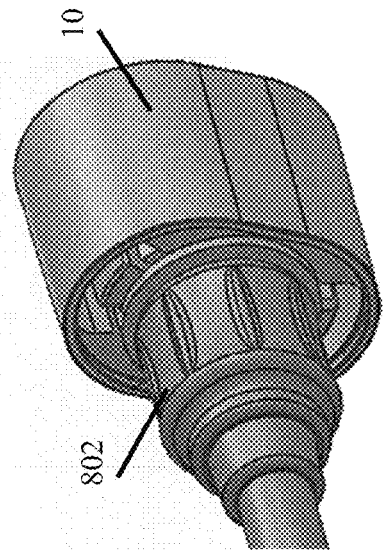
FIG. 8D is a bottom perspective view of the antimicrobial cap of FIG. 1 engaged with a medical port, in accordance with the disclosed subject matter.
Figure 8A:
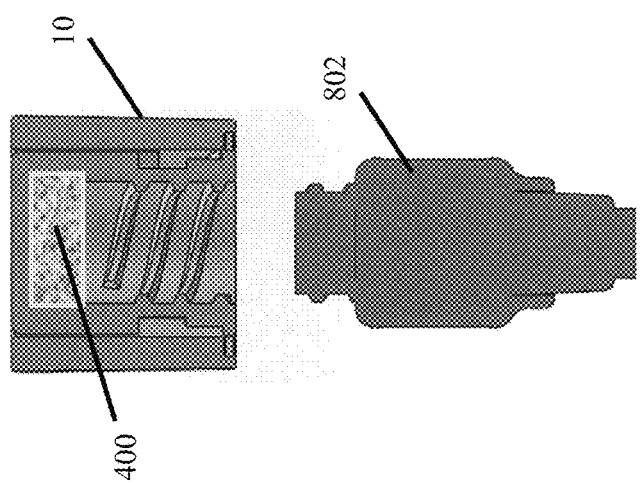
FIG. 8A is a side cross-sectional view of the antimicrobial cap of FIG. 1 with a medical port, in accordance with the disclosed subject matter.
Figure 8C:
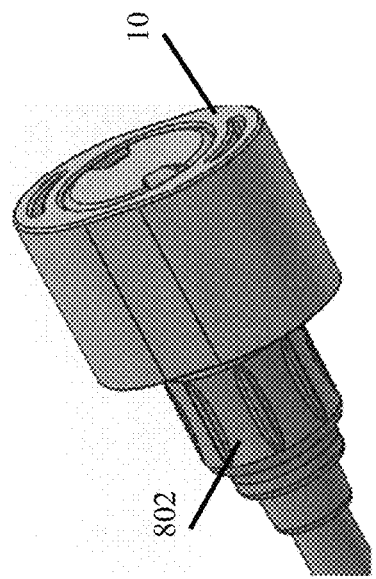
FIG. 8C is a top perspective side view of the antimicrobial cap of FIG. 1 engaged with a medical port, in accordance with the disclosed subject matter.

Solely for purpose of illustration, reference is now made to FIGS. 8A-8D showing different views of the assembled antimicrobial cap engaging a port for disinfection. FIG. 8A shows a side cross-sectional view of a line connected to medical port 802 that is ready to engage the assembled antimicrobial cap 10 by engaging a set of female threads disposed in the chamber of inner member 200. As shown, the inner member is disposed within the confines of the outer cap 10 indicating that the antimicrobial cap has not yet been utilized and a pad 400 having an antiseptic solution is disposed within the inner member. FIG. 8B shows a side perspective view of port 802 engaging the antimicrobial cap 10 during the disinfection process. FIG. 8C shows a top perspective side view of a line connected to medical port 802 engaging the antimicrobial cap 10 during the disinfection process. FIG. 8D shows a bottom perspective view of a line connected to medical port 802 engaging the inner member of antimicrobial cap 10 during the disinfection process.

Figure 9B:
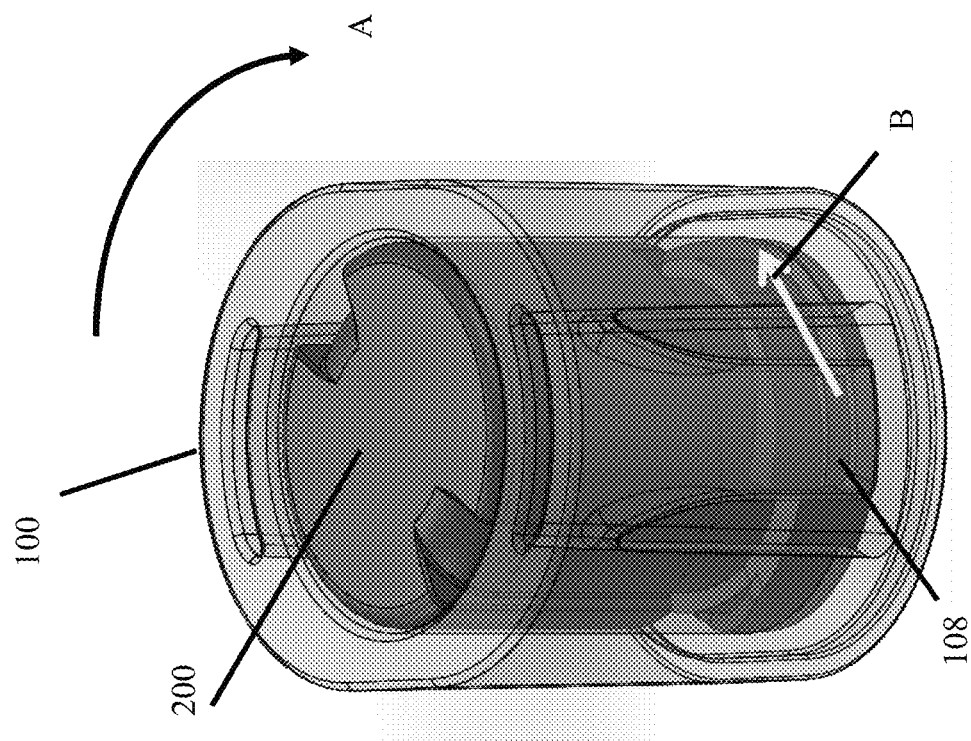
FIG. 9B is a side perspective view of the inner member of FIG. 1 with the outer cap in phantom in a first position in accordance with the disclosed subject matter.
Figure 9A:
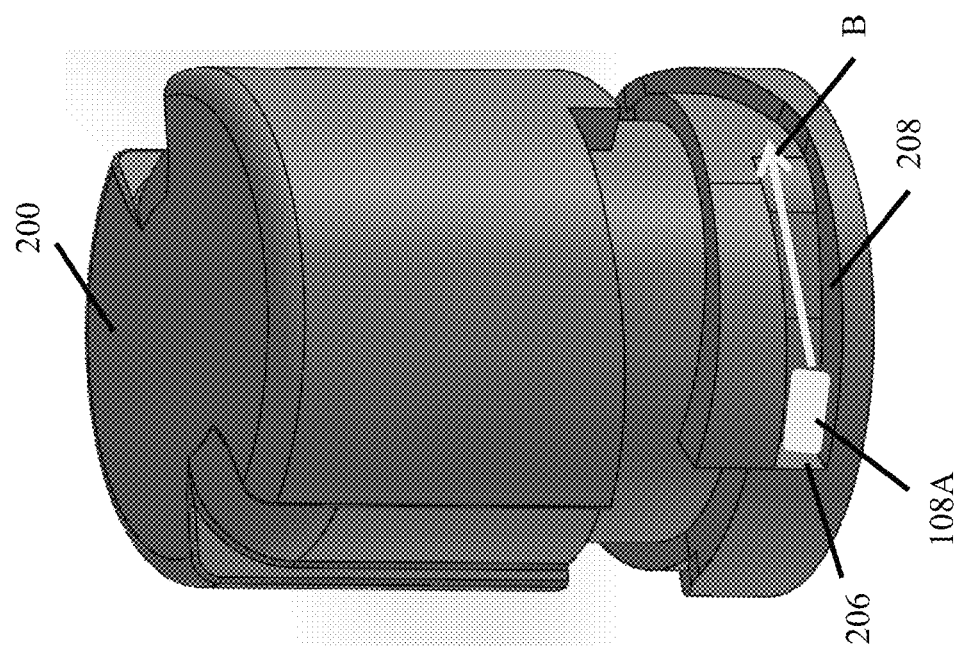
FIG. 9A is a side perspective view of the inner member of FIG. 1 in accordance with the disclosed subject matter.

Solely for purpose of illustration, reference is now made to FIGS. 9A-9B showing the antimicrobial cap and the relative positioning of the outer cap 100 with respect to the inner member 200 during the different stages of its use for disinfecting a port. Specifically, FIG. 9A shows the inner member 200 and an indication 108A of the initial position of the protrusion 108 of the flexural finger of outer cap 100 when the antimicrobial cap 10 is at a first position e.g., ready-to-use position upon removal from its packaging and prior to engaging a port. As discussed above in reference to FIG. 1, in the ready-to-use position, the pad containing the antimicrobial agent is disposed in the chamber 216 of inner member 200. The antimicrobial cap can be pushed onto a port then screwed onto the port such as in a first direction A, such as in a clockwise rotation of the cap onto the port. For purposes of example, the first direction A of the embodiment of FIGS. 9A-9B is clockwise, but it is understood that the antimicrobial cap can be manufactured such that a first direction is counter-clockwise. Moreover, with respect to the instant embodiment, for clockwise rotation, the protrusion 108 of the flexural finger 106 is engaged with the first stop 206 to permit the antimicrobial cap to screw on the port such that the outer cap and inner member move as a unit together with respect to the port (as shown with arrow A). As the outer cap 100 and inner member 200 move together in the first direction A, the inner member 200 can engage the threads of a port, and the port can engage with the pad 400 to release the antimicrobial agent therein in order to disinfect the port. FIG. 9B shows a perspective side view of the inner member 200 including the outer cap 100 shown in phantom. As illustrated therein, protrusion 108 abuts the first stop 206 located on the exterior surface of the inner member 200. As a result, the outer cap 100 can be rotated with respect to the inner member in a single direction A such that protrusion 108 moves along the first ramp 208. Once the antimicrobial cap 10 has been engaged with a port, the outer cap 100 can rotate with respect to the inner member 200 towards a second direction (shown with arrow B) e.g., counterclockwise to disengage the antimicrobial cap 10 from the port.

Figure 10B:
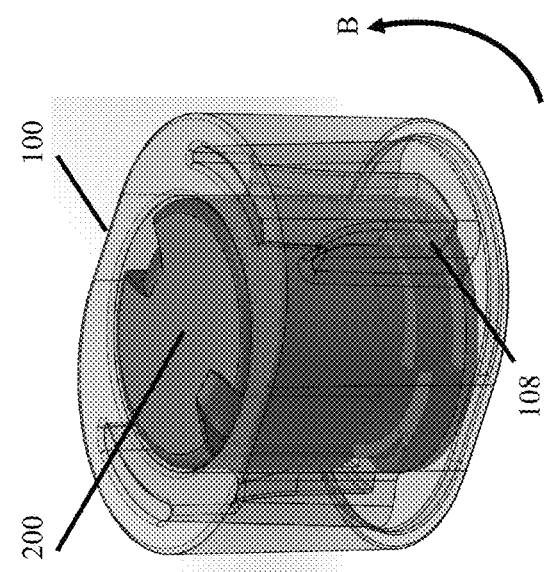
FIG. 10B is a side perspective view of the inner member of FIG. 9B with the outer cap in phantom moving toward a second position in accordance with the disclosed subject matter.
Figure 10C:
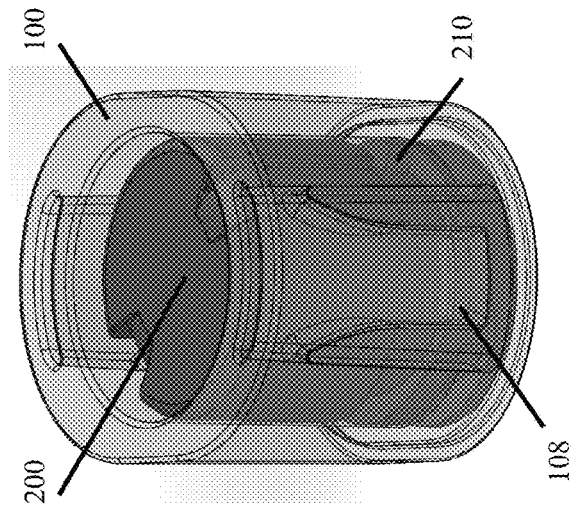
FIG. 10C is a side perspective view of the inner member of FIG. 10B in the second position in accordance with the disclosed subject matter.
Figure 10A:
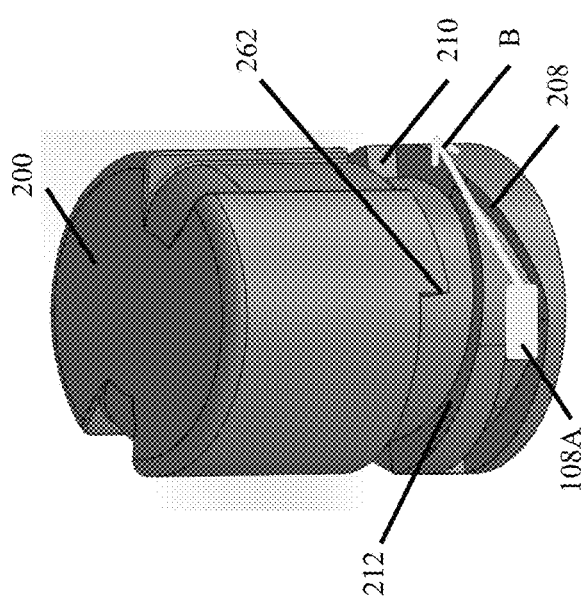
FIG. 10A is a side perspective view of the inner member of FIG. 9A rotated counterclockwise in accordance with the disclosed subject matter.

FIGS. 10A-10C show the inner member and outer cap at a position after use for disinfecting a port. Specifically, once a port is engaged with the inner member 200, as discussed in reference to FIGS. 9A-9B, the antimicrobial cap is detachable and is further rotatable with respect to the port in a second direction. Specifically, FIG. 10A shows the further direction of movement (shown with arrow B as indicated at 108A) of protrusion 108 of flexural finger 106 when the outer cap rotationally moves with respect to the inner member toward a second stop 210. For example, the outer cap is rotated in the second direction B, e.g., counterclockwise, as shown in FIG. 10B with the inner member stationary, and the protrusion 108 moves along the first ramp 208 in said direction. FIG. 10B shows where the protrusion 108 moves along the first ramp 208 as the outer cap 100 is rotated counterclockwise with respect to the inner member 200 until it reaches the second stop 210. As a result, once the protrusion 108 abuts the second stop 210 of the inner member, the outer cap can no longer continue its movement along the direction B without moving the inner member along therewith. In some embodiments, the second stop is located diametrically opposite the first stop 206. Alternatively, the second stop can be located at any suitable position along the exterior surface of inner member 200. In some embodiments, the second stop 210 is elevated with respect to the first stop 206 such that the second stop is disposed closer to the closed end 202 than the position of the first stop. FIG. 10C shows the protrusion 108 of the flexural finger 106 moving along second ramp 212 as the outer cap 100 is rotated back in the first direction A after abutting the second stop, as further discussed herein.

FIGS. 11A-11C show the inner member 200 and an indication 108A of the protrusion 108 of flexural finger 106 of the outer cap 100 at a position after using the cap for disinfecting a port and upon disengaging the cap of the port. Specifically, FIG. 11A shows the indication 108A of the protrusion 108 at the second stop 210 upon rotation of the outer cap 100 of the antimicrobial cap in the second direction B (e.g., counterclockwise). As shown in FIGS. 11B-11C, upon reaching the second stop 210, the indication 108A of the protrusion 108 abuts the second stop and as a result the outer cap 100 cannot be rotated any further towards the second direction B without then pushing the inner member in the direction B to remove the antimicrobial cap from the port. Once the protrusion 108 engages the second stop 210, the antimicrobial cap 10 can be removed from the port by exertion of further rotational force on the outer cap 100 to move the inner member 200 in the direction B. As such, the protrusion 108 has engaged and abutted the second stop 210. The movement of the outer cap 100 along the ramp 208 to the second stop 210 can cause the inner member to protrude out of the cavity of the outer cap, as shown in FIG. 12B and further discussed herein.

The flexural finger 106 is biased inwardly toward the center axis C such that the protrusion 108 maintains constant contact with the recessed exterior surface 224 of the sidewall of the inner member as the outer cap rotationally moves. At the location of the second stop 210, the recessed exterior surface 224 of the sidewall of the inner member is radially positioned closer to the axis C and the protrusion still maintains its contact with the recessed exterior surface 224 of the inner member due to its inwardly biasing nature. Due to such construction, the flexural finger and outer member is unable to move down the first ramp 208 back toward the first stop 206 after the outer cap 100 has been rotated in the second direction B and the protrusion 108 abuts the second stop 210. As such, the inner member 200 remains at least partially disposed outside of the outer cap 100, regardless of additional attempts at rotation in the first direction A, and is visually indicated as having been previously engaged with a port. In some embodiments, additional attempts at rotating the antimicrobial cap will permit the flexural finger 106 to continuously move along a second ramp 212 where it can abut a third stop 262 to engage the inner cap 200, as further discussed herein. In some embodiments, the second ramp 212 is radially distanced further inward than the first ramp 208 with respect to the center axis C of the antimicrobial cap. As a result, the flexural finger 106 cannot move down the first ramp 108 once it has reached the second stop 210 as the flexural finger 106 biases inwardly.

Figure 12B:
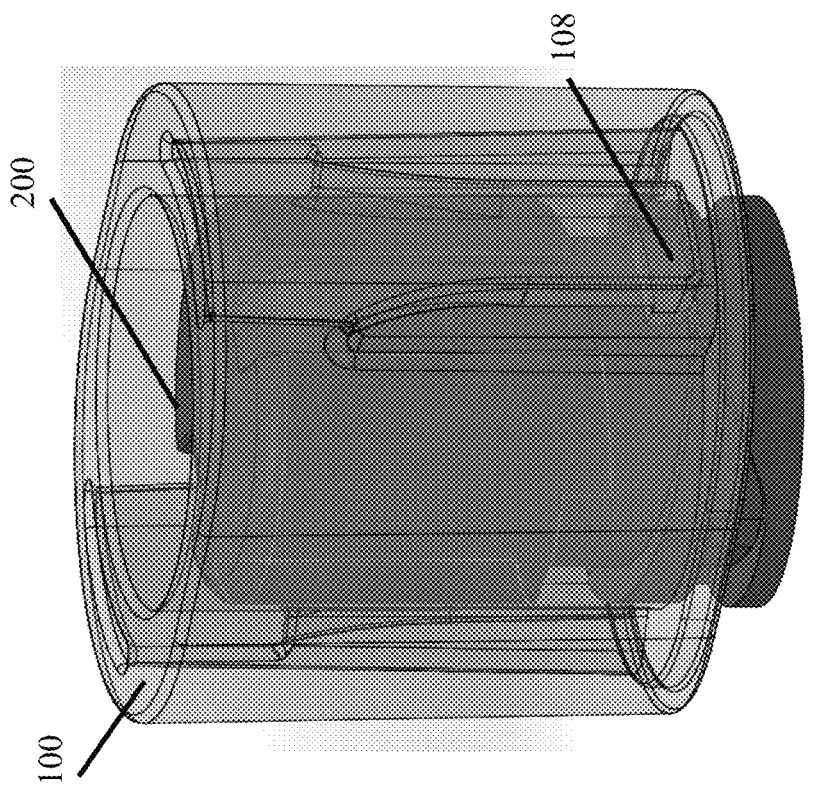
FIG. 12B is a side perspective view of the antimicrobial cap of FIG. 12A with the outer cap in phantom in accordance with the disclosed subject matter.
Figure 12A:
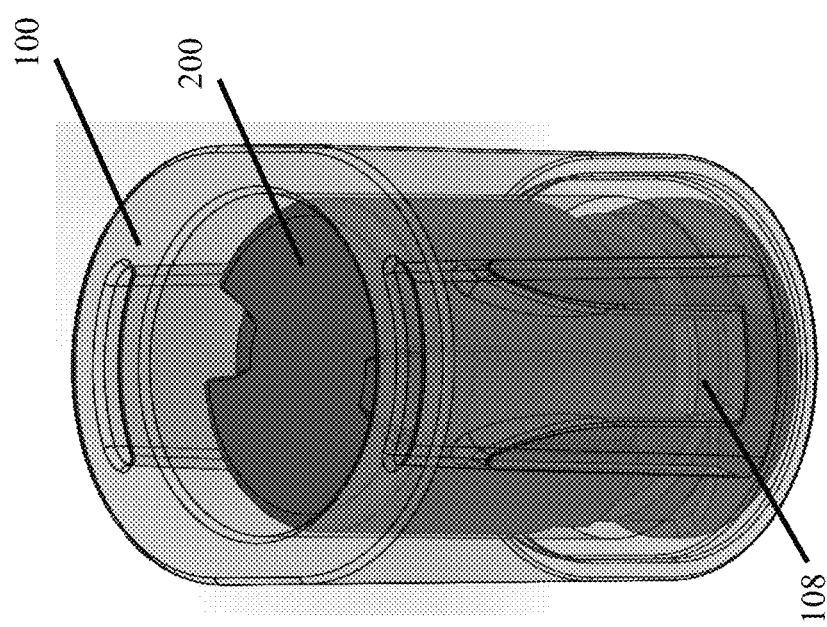
FIG. 12A is a top perspective view of the antimicrobial cap of FIG. 1 with the outer cap in phantom in a second position in accordance with the disclosed subject matter.

FIGS. 12A-12B show additional views of the antimicrobial cap. FIG. 12A shows a top perspective view of antimicrobial cap 10 with the outer cap 100 in phantom. Specifically, the port can become disengaged once flexural finger 108 of the outer cap 100 has moved along the first ramp 208 and reached the second stop 210. In some embodiments, the second stop 210 is located further elevated from the proximal end than the first stop 206, as previously referenced. As a result, the inner member 200 can become partially disposed outside the outer cap 100 hindering the antimicrobial cap from being reused, as previously discussed. FIG. 12B shows a side perspective view of the antimicrobial cap 10 with the outer cap 100 in phantom during disengagement of the port after disinfection. For example, as discussed above in connection with FIG. 12A, upon rotation of the antimicrobial cap towards a second direction B, the flexural finger 106 of the outer cap 100 moves along the first ramp 208 and abuts the second stop 210. Once the protrusion 108 of the flexural finger 106 reaches the second stop 210, the inner member 200 becomes at least partially released from the cavity and partially disposed outside of the outer cap 100 as shown. Moreover, further rotating the antimicrobial cap 10 in direction A causes the flexural finger 106 to move continuously along the second ramp 212 in the first direction A, preventing the outer cap 100 and the inner member 200 from moving together in direction A, and thus inhibiting the antimicrobial cap from further use as the inner member will not rotate on to the port. In some embodiments, the exterior surface of the inner member 200 includes a third stop 262. In certain embodiments the third stop 262 is located proximate the end of the second ramp 212 to permit the antimicrobial cap 10 to be disengaged from a port by further rotation of the outer cap in direction B, as described above. Referencing FIG. 11B, the protrusion 108 (as indicated by 108A) of the flexural finger 106 can move along the second ramp 212 to abut the third stop 262 and the inner member 200 continues to remain partially disposed outside the outer cap 100. In some embodiments, the outer cap 100 can be rotated at least 180° or any other suitable angle to disengage the engagement structure of the inner member 200 e.g., from male threads from the port.

Figure 13A:
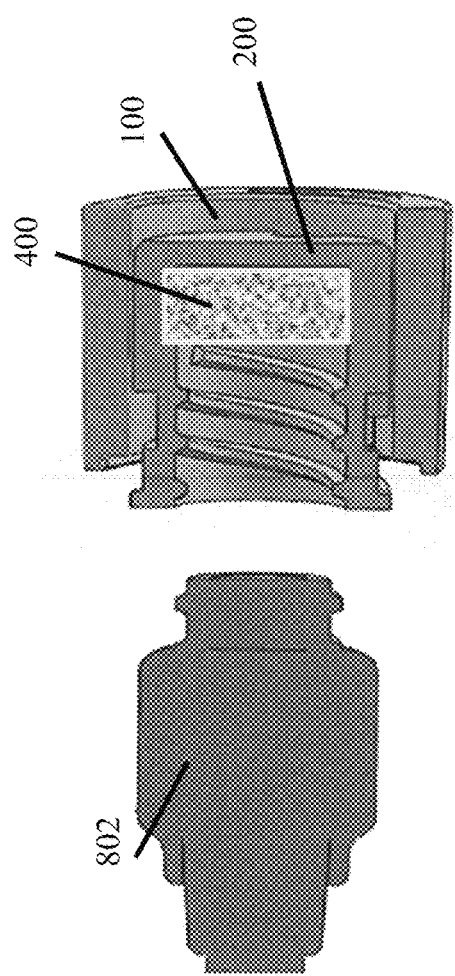
FIG. 13A is a side cross-sectional view of the antimicrobial cap of FIG. 1 disengaged from a medical port, in accordance with the disclosed subject matter.
Figure 13B:
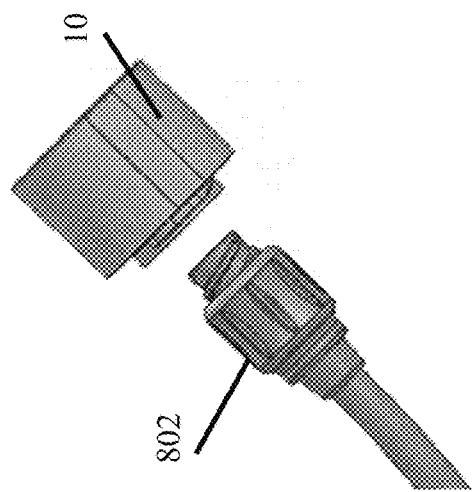
FIG. 13B is a side view of the antimicrobial cap of FIG. 13A disengaged from a medical port, in accordance with the disclosed subject matter.

Solely for purpose of illustration, reference is now made to FIGS. 13A-13B showing the antimicrobial cap 10 upon disengagement of the port 802. Specifically, FIG. 13A shows a side view of the port 802 and cross-sectional view of the antimicrobial cap 10 whereby the inner member 200 is partially disposed outside the outer cap 100. FIG. 13A further depicts the inner member 200 with a pad 400, therein. Similarly, FIG. 13B shows a side view of medical port 802 and antimicrobial cap 10 upon disengagement of the port where the inner member 200 is partially disposed outside the outer cap 100. As a result, the antimicrobial cap 10 is prevented from reapplication to medical port 802.

Accordingly, the antimicrobial cap 10 of the disclosed subject matter can be, and is preferably, configured as a single-use cap. After the antimicrobial cap 10 has been engaged with a port, subsequent removal of the antimicrobial cap 10 from the port results in a cap that cannot be reengaged to a port, and the cap provides a visual indication that it has been used. As such, re-use, including non-compliant re-use, of the antimicrobial cap 10 can be prevented. In some cases, such re-use of the antimicrobial cap can be in violation of industry and regulatory standards to ensure proper disinfection. For example, after a first use, the antimicrobial cap can become less effective due to exposure to the external environment, which can contaminate the cap and/or dry out antiseptic solution contained in the cap and thus can render the cap ineffective. Accordingly, the antimicrobial cap 10 can be, and is preferably, configured to prevent these and other risks associated with re-use activities.

In some embodiments, the pad contains any suitable antimicrobial element such as a disinfecting solution that disinfects the port upon contact. For example, in some embodiments, the antimicrobial element includes a solution such as alcohol, octenidine salts, chlorhexidine salts, aldehyde, anilide, silver compound, peroxygen, and or phenols or biguanides such as alexidine, phenoxyethanol, bis-phenols, quaternary ammonium compounds, PVP-iodine any cationic molecule, and/or mixtures such as chlorhexidine-silver or any suitable combination thereof. In some embodiments, the pad includes grooves, slots and/or cut-outs that align to the attachment features of inner member 200 in order to secure the placement of the pad 400.

The antimicrobial element contained within the pad can be suitable for any medical application. For instance, the fluid medium contained within the pad can be an antiseptic solution, and application of the solution to a portion of a body can kill microorganisms. In one embodiment, application of the antiseptic solution can kill microorganisms immediately and within approximately 10 minutes and further have a persistent effect for at least 7 hours. In some embodiments, the antiseptic solution can comprise at least one of chlorhexidine gluconate (CHG), isopropyl alcohol, purified water, and mixtures thereof. In another embodiment, the antiseptic solution can comprise at least 3.15% w/v chlorhexidine gluconate and 70% v/v isopropyl alcohol (both±10% w/v). The CHG can be designated as: 1, 1'---hexamethylenebis [5---(p---chlorophenyl)biguanide] digluconate, and have the following chemical structure:

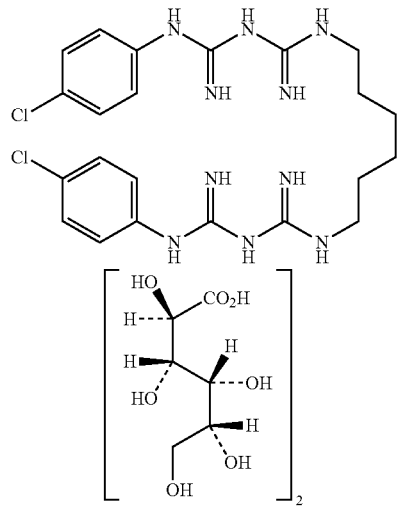

In accordance with another aspect of the disclosed subject matter, a method for inhibiting the growth of microbes and disinfecting a port, the method comprising providing an outer cap having a first end, a second end and defining a cavity therein, the outer cap having a sidewall with an inner surface that defines an engagement structure, an inner member receivable in the outer cap comprising an open end, a closed end and defining a chamber therein, the inner member having a sidewall with an interior surface and an exterior surface, wherein the interior surface is engageable with a port, the exterior surface defining an attachment feature configured to engage with the engagement structure of the outer cap, the attachment feature at least including a first stop, a second stop, and a first ramp there between, wherein the engagement structure abuts the first stop in a first position, a pad disposed within the chamber of the inner member, the pad impregnated with an antimicrobial agent. The method includes rotating the antimicrobial cap in a first direction with respect to the port to engage the inner member with the port, wherein the port is receivable in the chamber with the interior surface engaged thereto. The method includes compressing the pad by the port to release the antimicrobial agent therefrom, moving the engagement structure along the first ramp in a second direction and abutting the second stop in a second position, and rotating the antimicrobial cap with respect to the port and to release the antimicrobial cap from the port.

Figure 14B:
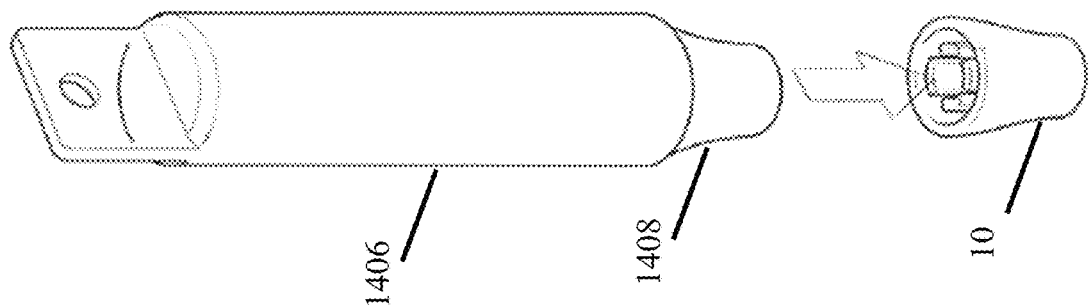
FIG. 14B is a side perspective view of a dispenser of the packaging for a plurality of antimicrobial caps of FIG. 6, in accordance with the disclosed subject matter.
Figure 14A:
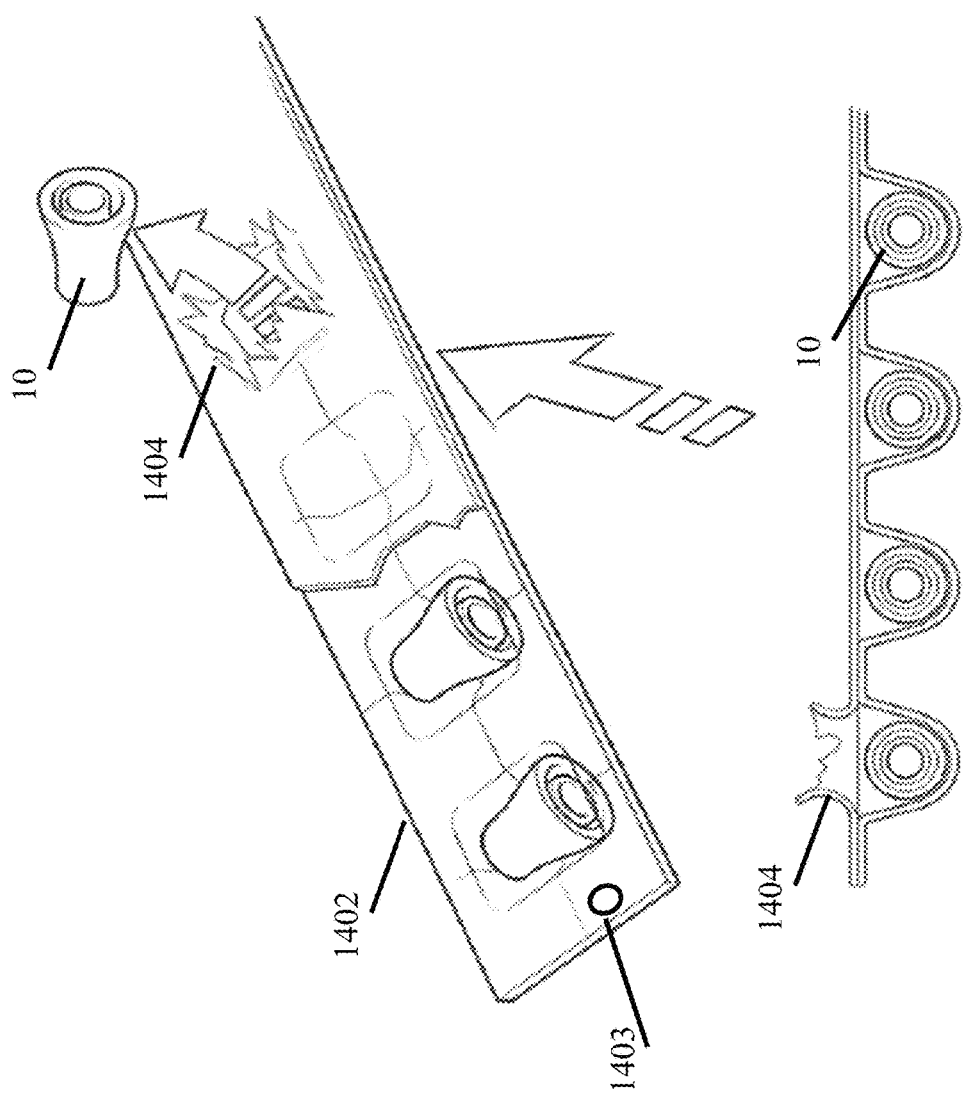
FIG. 14A is a top perspective view of a packaging for a plurality of antimicrobial caps, in accordance with an alternate embodiment.

FIG. 14A shows a plurality of antimicrobial caps each of them individually enclosed in blister pack 1402 and sealed using strip 1404. In some embodiments, the seal 1404 can be a foil/aluminum seal such that the antimicrobial caps can be dispensed through it from the blister pack 1402. In some embodiments the blister pack 1402 can include a hole 1403 for hanging/storage purposes as shown in FIG. 14A.

Figure 14E:
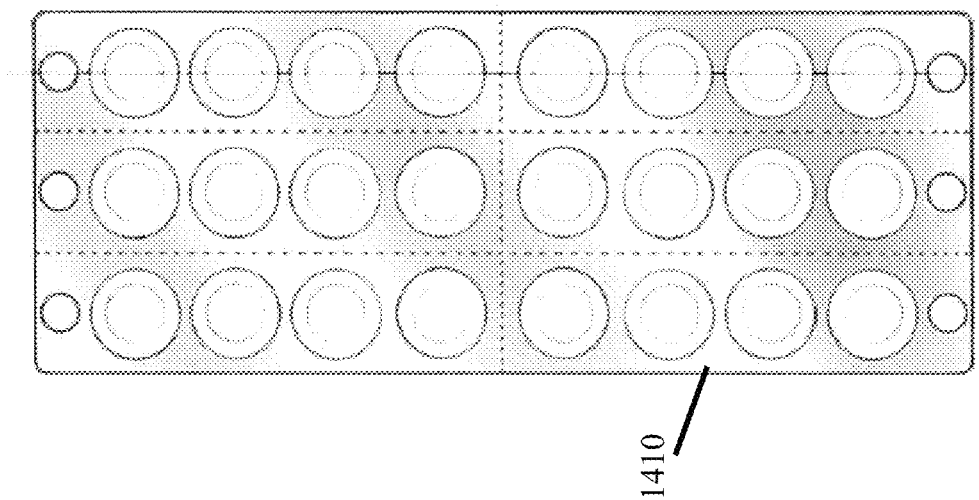
FIG. 14E is a top perspective view of a plurality of packagings of FIG. 14D, in accordance with the disclosed subject matter.
Figure 14D:
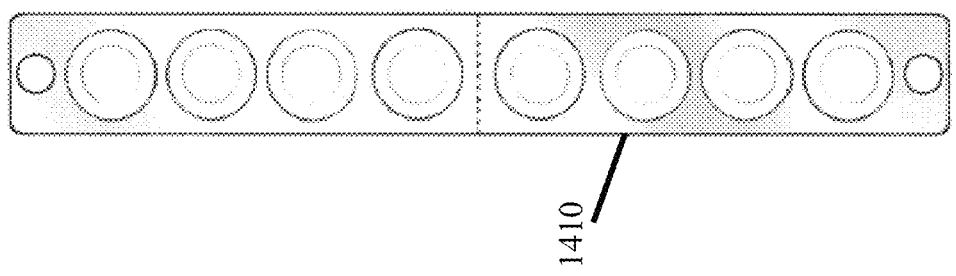
FIG. 14D is a top perspective view of a packaging for a plurality of antimicrobial caps, in accordance with an alternate embodiment.
Figure 14C:
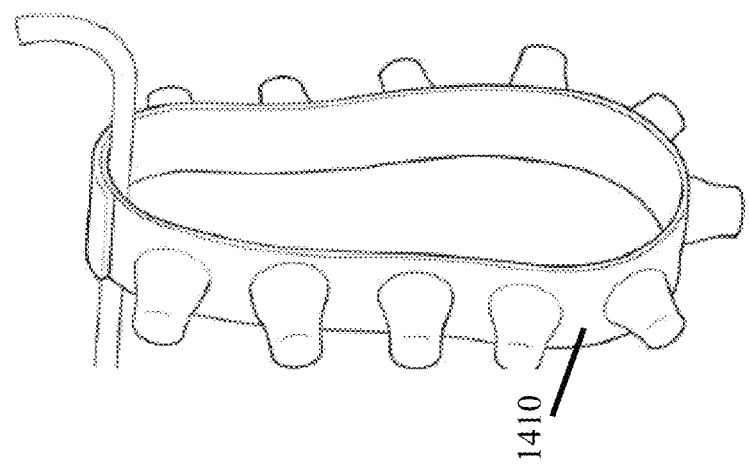
FIG. 14C is a side perspective view of a packaging for a plurality of antimicrobial caps, in accordance with an alternate embodiment.

FIG. 14B shows a side perspective view of an alternate packaging for a plurality of antimicrobial caps 10. Specifically, the packaging includes a dispenser sleeve 1406 that is capable of dispensing the antimicrobial caps 10 from nozzle 1408. Furthermore, the antimicrobial caps 10 of FIG. 14B can be sealed onto each other in the dispenser sleeve, such that a pull motion to the bottom antimicrobial cap also unseals the cap. In further embodiments, the antimicrobial caps 10 can be individually sealed when dispensed by dispenser sleeve 1406. In some embodiments, the dispenser or packaging can hang straight from an IV pole for ease of access, as shown in FIG. 14C. Additional configurations of strips are shown in FIGS. 14D and 14E. In FIG. 14D, a strip of four antimicrobial caps 1410 is coupled to a second strip of four antimicrobial caps by a perforation line. FIG. 14E depicts a series of strips coupled together about perforation lines. The number of antimicrobial caps per strip can vary as desired.

Figure 15:
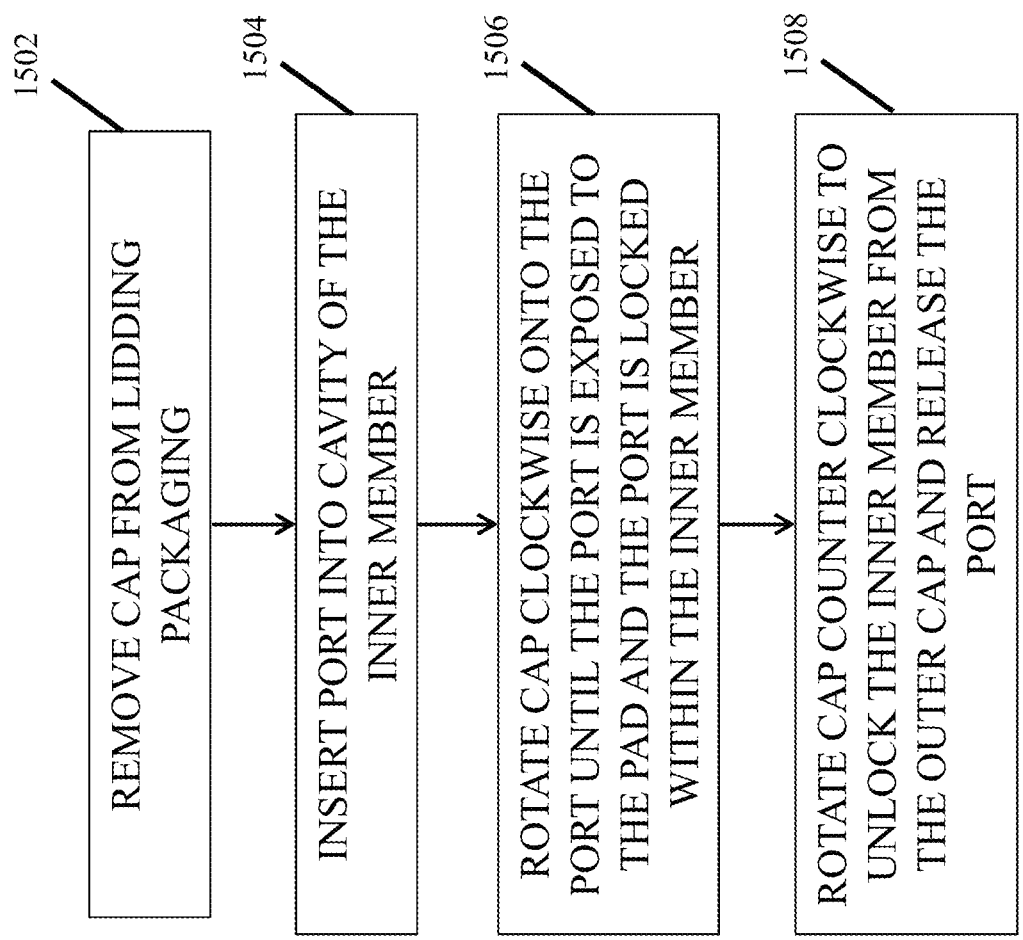
FIG. 15 illustrates a process for disinfecting a port using the antimicrobial cap of FIG. 1 in accordance with the disclosed subject matter.

FIG. 15 illustrates a process diagram for utilizing the antimicrobial cap and disinfecting a port using antimicrobial cap 10 in accordance with embodiments of the disclosed subject matter. Specifically, an antimicrobial cap is removed from the packaging lid or strip 602 to uncover the ready to use antimicrobial cap at 1502. At 1504, the port is inserted in the cavity of the inner member 200. In some embodiments, the inner member 200 is wholly disposed inside the outer cap 100 in the use condition. In some embodiments, the port engages a set of female threads 218 disposed along the inner surface of the inner member 200. Subsequently, at 1506 the antimicrobial cap is rotated and engaged with the chamber of inner member 200 until the port reaches the pad and becomes firmly seated within the inner member 200. The port can compress the pad and release the antimicrobial element from the pad in order to disinfect the port. Finally, at 1508, rotating the antimicrobial cap causes inner member 200 to rotate with respect to outer cap 100, and also rotates with respect to the port to release the port. As such, the flexural finger 108 of the outer cap 100 can move along the first ramp 208 and abut the second stop 210 to remove the cap from the port. Subsequently, the antimicrobial cap 10 can be rotated in further directions and the flexural finger can move along a second ramp 212 between the second stop 210 and a third stop 262. Such movement can cause the port to become disengaged from the antimicrobial cap indicating that the cap has been used as the inner member is partially dislodged from the cavity, while disabling the antimicrobial cap from reapplication.

While the disclosed subject matter is described herein in terms of certain preferred embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the various embodiments depicted and claimed, the disclosed subject matter is also directed to other embodiments having any other possible combination of the features disclosed and claimed herein. As such, the particular features presented herein can be combined with each other in other manners within the scope of the disclosed subject matter such that the disclosed subject matter includes any suitable combination of the features disclosed herein. Furthermore, although reference is made to a port throughout this disclosure, other suitable devices and connectors likewise can be disinfected using the antimicrobial cap and method disclosed herein. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method of the disclosed subject matter without departing from the spirit or scope of the disclosed subject matter. Thus, it is intended that the disclosed subject matter include modifications and variations that are within the scope of the appended claims and their equivalents.

What is claimed is:

1. An antimicrobial cap to treat a port, the antimicrobial cap comprising:
    an outer cap having a first end being an open end, a second end being a closed end, and defining a cavity therein, the outer cap having a sidewall with an inner surface that defines an engagement structure;
    an inner member receivable in the outer cap, the inner member comprising an open end, a closed end, and defining a chamber therein, the closed end of the inner member visible through the open end of the outer cap, the inner member having a sidewall with an interior surface and an exterior surface, wherein the interior surface is engageable with a port, the exterior surface defining an attachment feature configured to engage with the engagement structure of the outer cap, the attachment feature at least including a first stop, a second stop, and a first ramp there between, wherein the engagement structure abuts the first stop in a first position to permit rotational movement of the antimicrobial cap in a first direction with respect to the port and to engage the inner member with the port, wherein the engagement structure is movable with respect to the inner member along the first ramp in a second direction and abuts the second stop in a second position to rotate the antimicrobial cap with respect to the port and to release the antimicrobial cap from the port, wherein the engagement structure is movable along a second ramp of the attachment feature upon further rotating the antimicrobial cap in the first direction such that the engagement structure is prevented from further movement along the first ramp; and
    a pad disposed within the chamber of the inner member and impregnated with an antimicrobial agent, wherein the port is receivable in the chamber with the interior surface engaged thereto, wherein the pad is compressed by the port to release the antimicrobial agent therefrom.

2. The antimicrobial cap of claim 1, wherein the inner member is disposed within the outer cap in the first position.

3. The antimicrobial cap of claim 1, wherein the inner member is at least partially disposed outside the outer cap in the second position.

4. The antimicrobial cap of claim 1, wherein the first ramp of the attachment feature of the inner member is radially distanced further outward than the second ramp with respect to a longitudinal center of the antimicrobial cap.

5. The antimicrobial cap of claim 1, wherein the engagement structure of the outer cap comprises at least one flexural finger that inwardly biases against the exterior surface of the inner member and includes a protrusion at a distal end thereof, wherein the protrusion abuts the first stop and the exterior surface of the sidewall of the inner member, and wherein the protrusion moves along at least the first ramp to engage the second stop.

6. The antimicrobial cap of claim 5, wherein the engagement structure of the outer cap moves along the second ramp to abut a third stop.

7. The antimicrobial cap of claim 5, wherein the engagement structure of the outer cap and the attachment feature of the inner member are symmetrical about a longitudinal center of the antimicrobial cap.

8. The antimicrobial cap of claim 7, wherein the engagement structure of the outer cap further comprises at least a second flexural finger that inwardly biases against the exterior surface of the inner member and includes a protrusion at a distal end thereof, wherein the protrusion of the second flexural finger abuts a respective first stop and the exterior surface of the sidewall of the inner member, and wherein the protrusion of the second flexural finger moves along at least the respective first ramp to engage a respective second stop.

9. The antimicrobial cap of claim 8, wherein the second flexural finger moves along a respective second ramp to abut a respective third stop.

10. The antimicrobial cap of claim 7, wherein the respective first stops are distanced from each other by approximately 180° and wherein the antimicrobial cap is configured to be rotated clockwise to engage the inner member with the port.

11. The antimicrobial cap of claim 10, wherein the respective second stops are distanced from each other by approximately 180° and wherein the outer cap is configured to be rotated counterclockwise to disengage the inner member from the port.

12. The antimicrobial cap of claim 1, wherein the interior surface of the inner member comprises a plurality of female threads for engaging the port.

13. The antimicrobial cap of claim 12, wherein the outer cap is rotated counterclockwise to disengage the plurality of female threads of the interior surface of the inner member from the port.

14. The antimicrobial cap of claim 1 further comprising:
a lid coupled to a location of the antimicrobial cap to seal the cavity from an external environment, the location of the antimicrobial cap selected from a group consisting of a rim of the outer cap, a rim of the inner member, or a rim of the outer cap and a rim of the inner member.

15. The antimicrobial cap of claim 1, wherein the antimicrobial agent comprises at least one of alcohol, chlorhexidine gluconate, chlorhexidine-silver, and mixtures thereof.

16. A method for inhibiting the growth of microbes and disinfecting a port, the method comprising:
providing an outer cap having a first end being an open end, a second end being a closed end and defining a cavity therein, the outer cap having a sidewall with an inner surface that defines an engagement structure, an inner member receivable in the outer cap, the inner member comprising an open end, a closed end, and defining a chamber therein, the closed end of the inner member visible through the open end of the outer cap, the inner member having a sidewall with an interior surface and an exterior surface, wherein the interior surface is engageable with a port, the exterior surface defining an attachment feature configured to engage with the engagement structure of the outer cap, the attachment feature at least including a first stop, a second stop, and a first ramp there between, wherein the engagement structure abuts the first stop in a first position, a pad disposed within the chamber of the inner member, the pad impregnated with an antimicrobial agent;
rotating the antimicrobial cap in a first direction with respect to the port to engage the inner member with the port, wherein the port is receivable in the chamber with the interior surface engaged thereto;
compressing the pad by the port to release the antimicrobial agent therefrom;
moving the engagement structure along the first ramp in a second direction and abutting the second stop in a second position; and
rotating the antimicrobial cap with respect to the port and to release the antimicrobial cap from the port.

17. The method of claim 16 further comprising:
moving the engagement structure along a second ramp of the attachment feature upon further rotating the antimicrobial cap in the first direction such that the engagement structure is prevented from further movement along the first ramp and disengages the inner member from the outer cap.

18. The method of claim 16, wherein a lid is coupled to either a rim of the outer cap or a rim of the inner member or both a rim of the outer cap and a rim of the inner member to seal the cavity from an external environment, and wherein the method further includes removing the lid from the rim.

19. The method of claim 16, wherein the antimicrobial agent comprises at least one of alcohol, chlorhexidine gluconate, chlorhexidine-silver and mixtures thereof, wherein the method further comprises exposing the agent to the port.

20. The method of claim 16, wherein the engagement structure of the outer cap comprises at least a flexural finger that inwardly biases against the exterior surface of the inner member and includes a protrusion at a distal end thereof, wherein the protrusion abuts the first stop and the exterior surface of the sidewall of the inner member, and the method further includes moving the protrusion along at least the first ramp to engage the second stop and disengage the antimicrobial cap from the port.

* * * * *